(12) United States Patent
Green (10) Patent No.: US 11,162,892 B2
(45) Date of Patent: Nov. 2, 2021

(54) DEVICE AND METHOD FOR DETECTION OF COUNTERFEIT PHARMACEUTICALS

(71) Applicant: The United States of America, as represented by the Secretary, Department of Health & Human Services, Rockville, MD (US)

(72) Inventor: Michael D. Green, Atlanta, GA (US)

(73) Assignee: The USA, as represented by the Secretary, Dept. of Health and Human Services, Bethesda, MD (US)

( * ) Notice: Subject to any disclaimer, the term of this patent is extended or adjusted under 35 U.S.C. 154(b) by 679 days.

(21) Appl. No.: 16/071,843

(22) PCT Filed: Jan. 27, 2017

(86) PCT No.: PCT/US2017/015324
§ 371 (c)(1),
(2) Date: Jul. 20, 2018

(87) PCT Pub. No.: WO2017/132502
PCT Pub. Date: Aug. 3, 2017

(65) Prior Publication Data
US 2021/0208063 A1     Jul. 8, 2021

Related U.S. Application Data (60) Provisional application No. 62/287,711, filed on Jan. 27, 2016.

(51) Int. Cl.
*G01J 5/02* (2006.01)
*G01N 21/3563* (2014.01)
(Continued)

(52) U.S. Cl.
CPC ......... *G01N 21/3563* (2013.01); *G01N 21/63* (2013.01); *G01N 21/9508* (2013.01); *G01N 2201/0221* (2013.01)

(58) Field of Classification Search
CPC ............... G01N 21/3563; G01N 21/63; G01N 21/9508; G01N 2201/0221
See application file for complete search history.

(56) References Cited

U.S. PATENT DOCUMENTS 4,295,042 A    10/1981  Watanabe et al.
5,104,228 A *  4/1992   Baillie ................. G01N 21/534
                                                   250/576
(Continued)

OTHER PUBLICATIONS

International Search Report and Written Opinion of the International Searaching Authority issued in corresponding International Patent Application No. PCT/US2017/015324 dated Apr. 18, 2017.
(Continued)

*Primary Examiner* — Kiho Kim
(74) *Attorney, Agent, or Firm* — Sheridan Ross P.C.

(57) ABSTRACT

A device (100) for measuring light transmission through a suspected counterfeit pharmaceutical tablet (102) includes a laser source (110) configured to emit a light transmission through the pharmaceutical tablet (102). A light detector (120) is included in the device (100) configured to receive the light transmission and measure an amount of light passed through the suspected counterfeit pharmaceutical tablet (102). The amount of light transmitted through the suspected counterfeit pharmaceutical tablet (102) is indicative of an authentic or counterfeit.

14 Claims, 7 Drawing Sheets

(51) Int. Cl.
 *G01N 21/63* (2006.01)
 *G01N 21/95* (2006.01)

(56) References Cited

U.S. PATENT DOCUMENTS

| | | | |
|---|---|---|---|
| 9,312,701 B1* | 4/2016 | Mor | H02J 5/005 |
| 9,908,217 B2* | 3/2018 | Sarangi | B24D 3/18 |
| 2012/0013734 A1 | 1/2012 | Ranieri et al. | |
| 2013/0256534 A1 | 10/2013 | Micheels et al. | |
| 2013/0284930 A1* | 10/2013 | Kato | G01N 21/3581 |
| | | | 250/341.1 |
| 2014/0183362 A1 | 7/2014 | Islam | |
| 2014/0354989 A1 | 12/2014 | Marbach et al. | |

OTHER PUBLICATIONS

Neil A MacLeod et al: "Emerging Non-invasive Raman Methods in Process Control and Forensic Applications", Pharmaceutical Research, Kluwer Academic Publishers-Plenum Publishers, NL, vol. 25, No. 10, Apr. 16, 2008 (Apr. 16, 2008), pp. 2205-2215.

* cited by examiner

Color absorbance properties of various antimalarial drugs

DEVICE AND METHOD FOR DETECTION OF COUNTERFEIT PHARMACEUTICALS

CROSS REFERENCE TO RELATED APPLICATIONS

This application claims the benefit of U.S. Provisional Patent Application Ser. No. 62/287,711 filed Jan. 27, 2016, which is expressly incorporated by reference herein.

STATEMENT REGARDING GOVERNMENTAL SUPPORT

The present subject matter was made with U.S. government support. The U.S. government has certain rights in this subject matter.

FIELD OF INVENTION

The present invention generally relates to methods and devices for the detection of counterfeit pharmaceuticals and/or the packaging therefore and more particularly to devices and methods for detection of counterfeit pharmaceuticals and/or counterfeit packaging using visible and non-visible radiation and yet more particularly to devices and methods for in-situ detection of counterfeit pharmaceuticals using visible and non-visible radiation.

BACKGROUND OF THE INVENTION

The proliferation of counterfeit pharmaceuticals is a serious public health issue. These drugs may not contain the active ingredient, may contain the wrong active ingredient, or may contain the active ingredients in suboptimal doses. Counterfeits may also contain toxic ingredients. Counterfeiters have targeted developing countries where drug regulatory agencies lack resources to properly monitor and ensure good drug quality. Sophisticated and analytical equipment, such as high-performance liquid chromatography (HPLC) with mass spectrometric or diode array detectors are standard equipment for drug analysis, but are scarce in developing countries due to high cost. Maintaining these instruments is also problematic due to lack of expertise as well as scarce resources.

Current methods for detecting counterfeit pharmaceuticals include vibrational spectroscopy, x-ray diffraction, gas chromatography, liquid chromatography and mass spectrometry. These methods, although often effective, require expensive and bulky instrumentation, and are generally performed in a laboratory.

It thus would be desirable to provide new devices and methods for detecting counterfeit pharmaceuticals and/or packaging from the pharmaceuticals and/or packaging from an authorized manufacturer, supplier and the like. It would be particularly desirable to provide such devices and methods that would be portable and usable at any desired location such as the inspection point for customs. It also would be particularly desirable to provide such devices that would be hand-held and use visible and/or non-visible light to illuminate suspect pharmaceuticals and/or packaging and determining from such illumination if the pharmaceuticals and/or packaging being examined are counterfeit pharmaceuticals and/or packaging. Such detection devices preferably would be simple in construction and less costly than prior art devices and such methods would not require highly skilled users to utilize the device.

SUMMARY OF THE INVENTION

A device for measuring light transmission through a suspected counterfeit pharmaceutical tablet includes a laser source configured to emit a light transmission through a suspected counterfeit pharmaceutical tablet and a light detector configured to receive the light transmission and measure an amount of light passed through the suspected counterfeit pharmaceutical tablet. The amount of light transmitted through the suspected counterfeit pharmaceutical tablet or the color (frequency) of light emitted from the tablet is indicative of an authentic, counterfeit or degraded pharmaceutical tablet (solid dosage form). In most instances when the amount of light measured through the suspected counterfeit pharmaceutical tablet is significantly different than a known amount of light measured through an authentic sample indicates a counterfeit. In addition, the change in color of light emitted from a sample tablet relative to an authentic tablet can also indicate a counterfeited or degraded tablet.

A plurality of colored or infrared filters of varying wavelengths can be included to condition the light emitted from the suspected counterfeit pharmaceutical tablet. The light detector can include a photo sensor in electronic communication with a meter configured to measure electrical current as a function of the light transmission and convert the measured light transmission to a quantifiable or semi-quantifiable output. Examples of such outputs include but not limited to an analogue meter, digital readout, LED indicator or sound. The photo sensor can be a CdS photoresistor photodiode, phototransistor, photovoltaic cell, or charged coupled device in electronic communication with an electronic output (i.e., a meter) configured to measure the light transmission (or emission) and convert the measured light transmission to a quantifiable output. The light detector can include a photoresister in electronic communication with an ohmmeter or digital voltmeter configured to measure the intensity of the light passed through the suspected counterfeit pharmaceutical tablet. A charged couple device (CCD), typically found in digital cameras, along with image analysis software, may also be used to measure the intensity and color of light passing through a sample tablet.

The device can further include a tablet interface configured to secure the suspected counterfeit pharmaceutical tablet between the laser source and light detector. The interface can include an O-ring surrounding the suspected counterfeit pharmaceutical tablet configured to block extraneous light and concentrate light from the laser source to pass through the tablet.

The suspected counterfeit pharmaceutical tablet can include a molded and compressed solid dose pharmaceutical tablet. The light source can include a wavelength in the range of class IIIa (<5 mW) or class IIIb (5-500 mW). The light detector can include an inlet configured to communicate with a power source.

A method for measuring light transmission through a suspected counterfeit pharmaceutical tablet includes providing the device as described above and directing the laser source towards a suspected counterfeit pharmaceutical tablet. The intensity of the emitted light transmission is concentrated through the suspected counterfeit pharmaceutical tablet towards the laser detector. The intensity of the light transmission is measured through the suspected counterfeit pharmaceutical tablet using a photo sensor in electronic communication with a meter. The measured light intensity is compared to a known intensity of an authentic tablet to determine the authenticity of the suspected counterfeit pharmaceutical tablet.

BRIEF DESCRIPTION OF THE DRAWING

So that those having ordinary skill in the art to which the disclosed system appertains will more readily understand how to make and use the same, reference may be had to the drawings wherein.

DETAILED DESCRIPTION OF THE PREFERRED EMBODIMENTS

For a fuller understanding of the nature and desired objects of the present invention, reference is made to the following detailed description taken in conjunction with the accompanying drawing figures wherein like reference character denote corresponding parts throughout the several views.

The present disclosure includes devices and methods for the detection of suspected counterfeit pharmaceuticals (i.e. tablets). Such methods include exposing a suspected counterfeit tablet to a light source and measuring the amount of light transmission through the suspected counterfeit tablet. The device, embodying such methods, is portable and includes a light source to generate the light to which the suspected counterfeit tablet is exposed and a measuring device to measure the amount of light transmitted through the suspected counterfeit tablet.

The device shall be referred to as the Counterfeit Drug Identifier or CoDI and in certain embodiments includes three main components: 1) a laser light source; 2) a light detector; and 3) sample holder. The CoDI can be a single device, housing all three components or a kit comprised of separate components, the combination thereof designed for measuring relative light transmission (or absorbance) through a suspected counterfeit pharmaceutical solid dosage form, (e.g. tablet). In some cases the light intensity emanating from the tablet may be enhanced as a result of fluorescence.

The suspected counterfeit tablet is identified when the amount of light transmission is measured through the use of the measuring device. The intensity and color (frequency or wavelength) of light transmitted through or emitted from the suspected counterfeit pharmaceutical tablet relative to an authentic, unexpired reference tablet is indicative of an authentic or counterfeit pharmaceutical tablet. More specifically, each brand of tablet is formulated with a characteristic blend of active and inactive ingredients (excipients). Drug manufacturers produce tablets of particular sizes and shapes to distinguish their brand from that of other manufacturer's. Therefore, each brand of tablet has characteristic properties, i.e., density, color inscriptions, shape and thickness.

The combination of these properties affects light transmission through the tablet. Tablet thickness and density attenuate the intensity of the light while particular chemicals present in the tablet can alter the wavelength of light as it passes through the material. Counterfeit tablets are usually produced from commonly found materials such as chalk, flour, or starch or reformulated from expired products. The resulting tablet may look exactly like the genuine but exhibit different physical properties. It has been noted that variability between genuine pharmaceutical tablets are minimal since the production processes of such products are highly controlled. Thus, the appearance of different lots of such genuine tablets will be very similar when viewed under different wavelengths of lights. In contrast, suspect counterfeit tablets do not have a single source, are not controlled as highly in the various sources and consequently have a greater variability in appearance and will generally appear different from genuine products.

Figure 1:
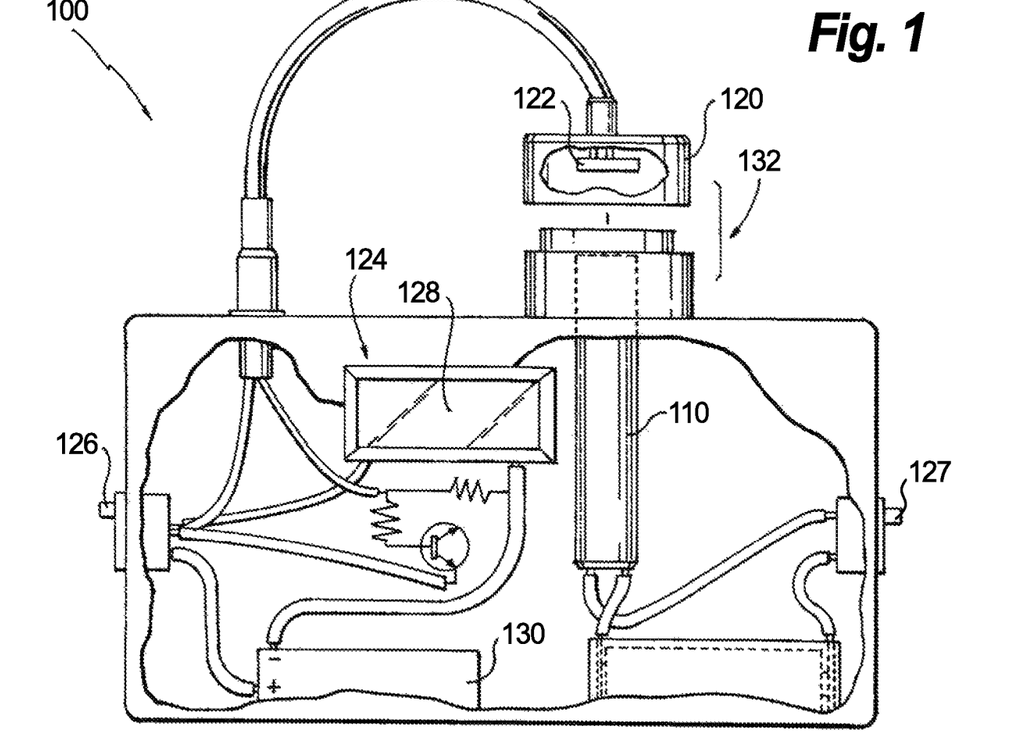
FIG. 1 is a schematic diagram illustrating an exemplary embodiment of a working device designed with multiple components, including a tablet holder and light detector, necessary for detecting counterfeit pharmaceuticals in a single housing.

Referring now to the various figures wherein like reference characters refer to like parts, a schematic diagram of the device is shown in FIG. 1. The device 100, a counterfeit drug indicator, is an inexpensive portable screening device and method for determining whether a tablet 102 (shown in FIG. 2) of unknown origin is legitimate or not. The device 100 includes a laser source 110 configured to emit a light transmission through the tablet 102 and a light detector 120 configured to receive the light transmission and measure an amount of light passed through the tablet 102. The laser source 110 can be a hand-held, commercially available laser or a module consisting of a laser diode and driver.

Figure 3:
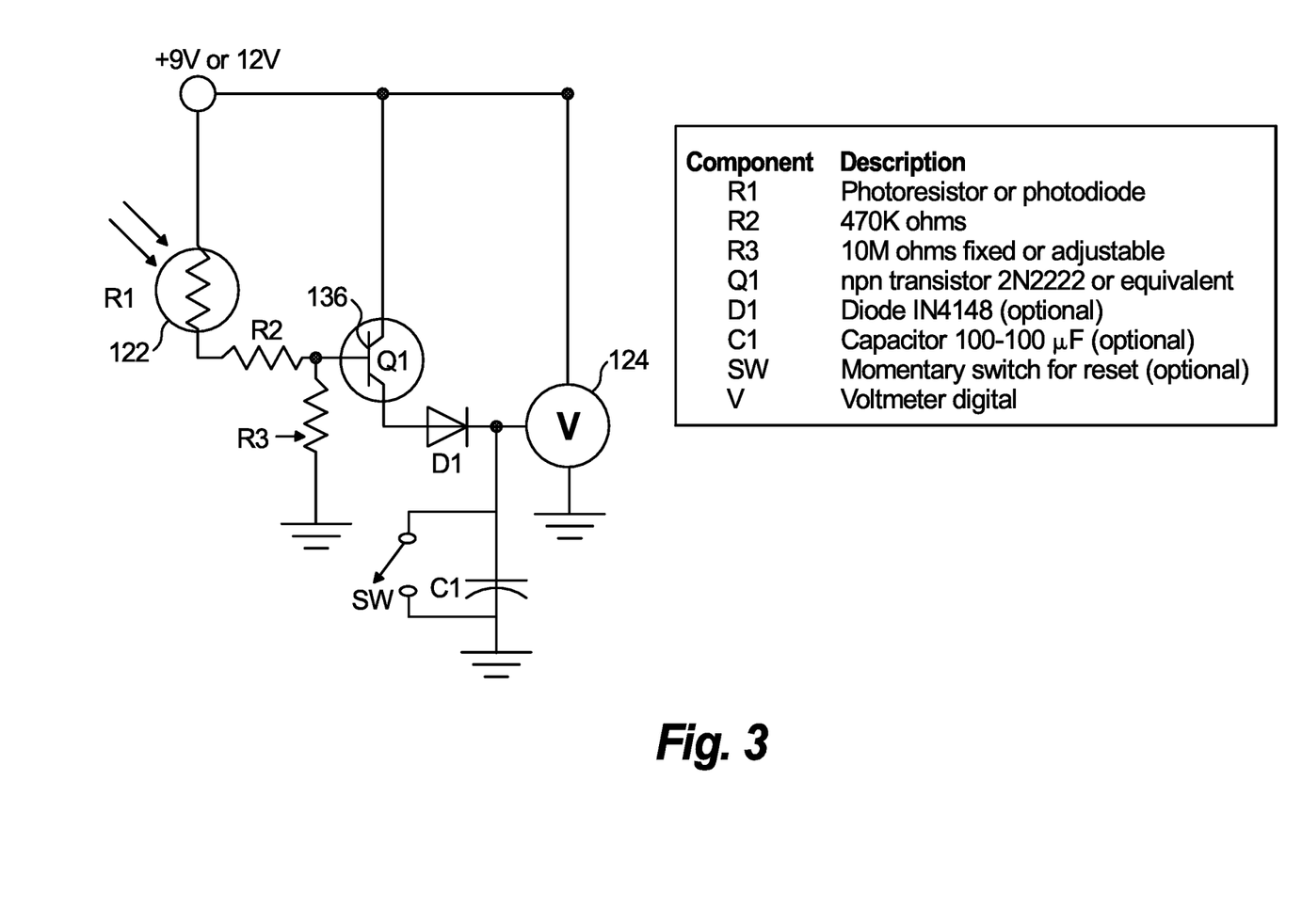
FIG. 3 is a schematic diagram of an exemplary embodiment of internal circuitry of the light detector of FIG. 1.

The power requirements of the laser source 110 depends on the sensitivity of the light detector 120 used in conjunction therewith. For example, FIG. 3 shows the internal circuitry for a light detector 120 using a photoresister 122 and voltmeter 124 with higher sensitivity that is suitable for a laser with low power, e.g., class IIIa<5 mW or class IIIb (5-500 mW). In alternate embodiments, a camera taking digital photos of tablets exposed to high power, e.g., 200 mW, laser light may be assessed using image analysis software to determine authenticity.

With continued reference to FIG. 1, the light detector 120 can include, among other features, an on/off power switch 126 for the laser detector 120, an on/off power switch 127 for the light source 110, and a visual display 128. The switches, buttons or control keys can be implemented as physical hardware components and/or software elements. Alternatively, the device may embody any of a number of other devices or techniques as is known to those skilled in the art than can control the light detector.

The light detector further includes communication to a power source 130. Such a power source 130 is any of a number of sources of electrical power as is known to those skilled in the art and including for example rechargeable or non-rechargeable batteries (e.g., alkaline, lithium ion, metal hydride and the like) and capacitors or high power capacitors. Such power sources 130 also can further include any of a number of electrical functionalities known to those skilled in the art (e.g., transformers) so as to control the power (voltage, current) being outputted by the power source so as to be at or about an appropriate value. In more particular embodiments, the device 100 is constructed so as to be made in a hand-held form and be portable. In further illustrative embodiments, the power source 130 is a battery such as a 9V DC portable battery.

Figure 2:
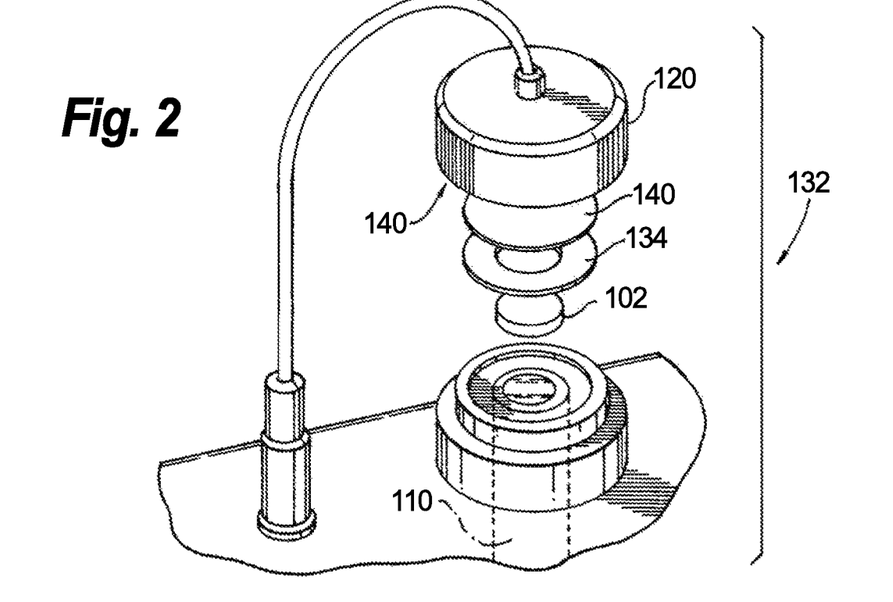
FIG. 2 is a schematic diagram illustrating the tablet holder of the device of FIG. 1, which is designed to position the tablet at the interface of a laser light source and the light detector.

With reference to FIG. 2, the device 100 further includes a sample tablet holder/interface 132 where a suspected counterfeit tablet is positioned between the laser source 110 and light detector 120. The interface 132 is constructed such that light transmission through the tablet 102 and acquisition by the photoresister 122 (shown in FIG. 1) is optimized and extraneous light is blocked by a flexible, light-impervious O-ring 134 surrounding the periphery of the tablet 102, allowing only the laser light to pass through the tablet 102. The photoresistor 122 is placed over an opposing side of the tablet 102 such that only light emanating from the laser is transmitted through the tablet 102, which is subsequently detected and measured. The interface 132 allows the light transmission to reach the designated components to measure the amount of light. In other embodiments, the sample tablet may also be "sandwiched" between two flexible light-impervious materials with an opening to allow the laser light to pass through the sample tablet and be detected As mentioned, various embodiments of the light detector 120 are contemplated that include circuit components or elements that can carry out the functions described herein, including, a light meter, a digital camera, a photocell, a photoresistor, photodiode or charged-couple device (CCD). In additional embodiments the light detector 120 can include an analog or digital meter used to measure electrical current passing through a photo sensor as a function of light intensity emanating from a tablet exposed to the laser light source.

FIG. 3 shows an exemplary embodiment of internal circuitry for the light detector 120 with the present device 100. This circuit is used to amplify the current passing through the photo sensor suited for lower power laser light, which are typically safer and more affordable. In FIG. 3, the circuitry for the light detector 120 is more user-friendly and may further reduce signal drift and provide a more consistent result. The circuit in FIG. 3 uses a transistor 136 to amplify the current passing through the photoresistor 122. Integrated circuits may also be employed to enhance signal strength. The sensitivity of the light detector 120 is influenced by the relative resistance of R2 and R3 and can be manipulated by substituting R3 with a potentiometer. A capacitor C1 may be used to increase signal stability.

Referring to FIG. 2, a plurality of colored or infrared filters 140 are included to further aid in identification based on the physical properties of the tablet 102. The thickness and density of the tablet 102 determines how much light is able to go through the tablet 102. Since many materials fluoresce when exposed to a violet (405 nm laser) light source, filters 140 are used to give the method more specificity. For example, genuine Coartem tablets transmit orange light when violet laser light passes through it. When laser light passes through a fake Coartem tablet, it may be totally blocked due to tablet density or thickness, or may absorb or fluoresce in a different region of the light spectrum. Therefore, colored filters outside the orange spectral range such as a blue, green or red filter may be used to better identify a counterfeited tablet. If an authentic tablet transmits orange light, then blue, green and red light is being absorbed by the sample tablet.

Figure 4:
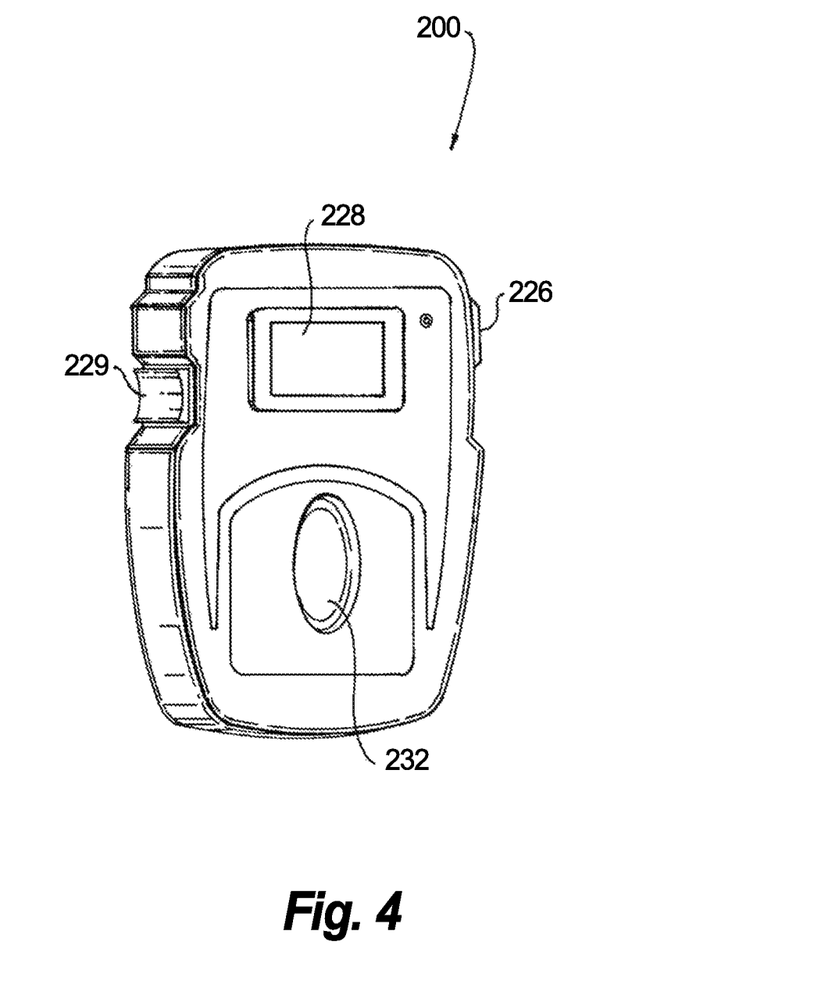
FIG. 4 is another exemplary embodiment of a working device for detecting counterfeit pharmaceuticals in a single housing.

FIG. 4 illustrates another embodiment of the counterfeit drug indicator device 200. This embodiment includes the same circuitry as shown in FIG. 3, however, the features of the device 200 are housed in a relatively compact and easy to hold device 200. As shown device 200 similarly includes a display screen 228 with an on/off switch 229, a power switch 226 for operation of the laser and a sample compartment holder 232 with an easy to access front loading pill holder. While not shown, the device 200 can include additional features for ease of use. For example, and LED indicator to indicate when the testing is active and a back compartment to store additional pills/tablets. The sample compartment holder 232 can include built-in color filters 140 and/or diffuser filters. Further, the cover of the holder 232 can seal out ambient light and provide a water resistant seal.

Devices 100 and 200 are designed to be used easily and quickly to identify suspected counterfeit tablets. Devices 100 and 200 are portable and lightweight, thus, it is well suited for work in the field, at border locations and at customs counter. The devices 100, 200 obviate the need to send field samples to a laboratory for analysis and does not require consumables, i.e. solvents or chemicals that can destroy the samples. Thus, customs agents or drug regulatory agents can quickly determine whether a suspect pharmaceutical is in fact counterfeit. If desired, the suspected counterfeit pharmaceutical can be subjected to further confirmatory testing using conventional methods.

The devices 100, 200 can also include wireless capability and tracking to further enhance data collection and location of increased counterfeit drug activity. For example, each device can be equipped with Bluetooth, Wi-Fi capability and integrated GPS. This would allow the devices 100, 200 transmit values and locations to a central database for future reference. Results can also be sent to a smartphone to aid drug enforcement agencies in locating fake drug production facilities. Each device 100, 200 may further be equipped with theft protection such as unique individual unit identification technology, GEO-tagging of unit location, or stolen device deactivation features.

Figure 5:
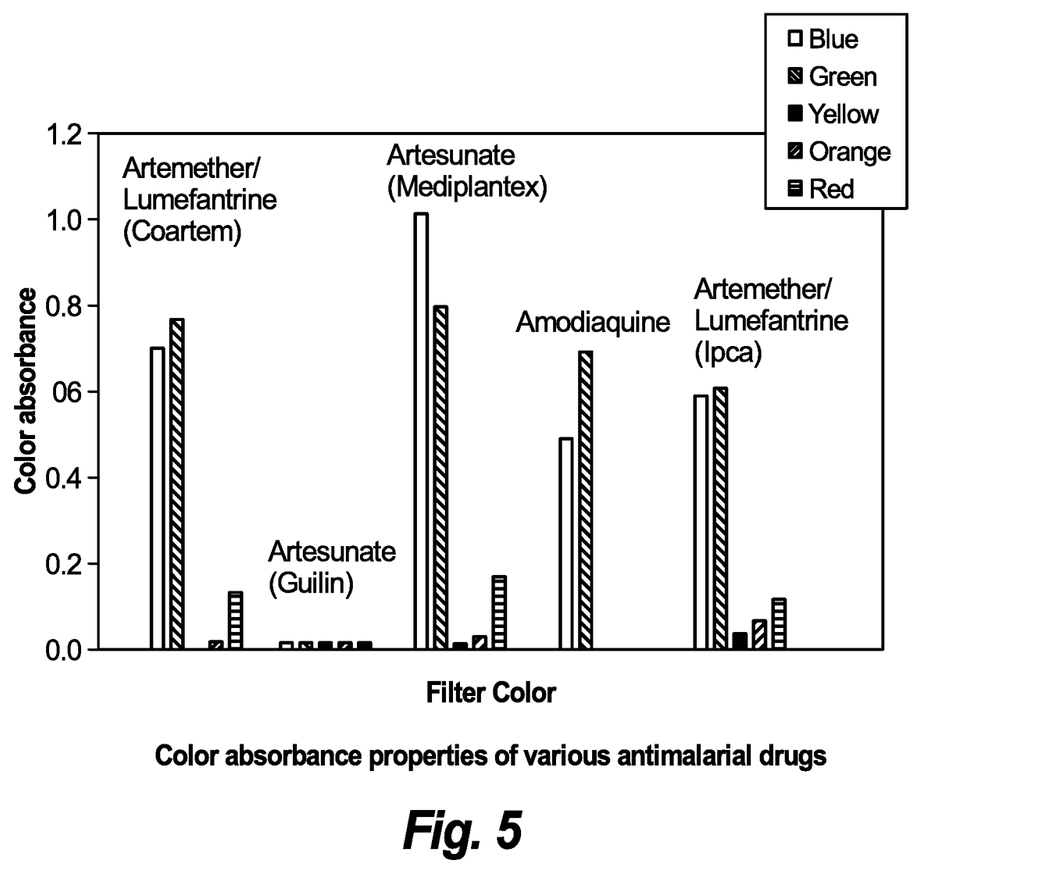
FIG. 5 is a bar graph illustrating the responses of various antimalarial drugs with transmitted laser light using different colored filters of the device of FIG. 1.

FIG. 5 illustrates the color absorbing properties of various brands of antimalarial drugs. A blue, green or red filter is selected to better distinguish counterfeited tablets from authentic. Also, filters that transmit infrared light may be used to distinguish a counterfeited tablet. It is within the scope of the present invention to establish criterion and operating protocols to follow that allow one to determine the color of such filter for viewing a suspect product to see if it is an authentic product. For example, it may be established from a series of experiments that, to determine whether an unknown tablet purportedly from Manufacturer A is counterfeit, the suspect product should be viewed under a blue filter. Thus, when a suspect product when viewed under such conditions emits light different from a known authentic tablet with the same filter one can conclude that the suspect product is a counterfeit. Prior to using the CoDI to identify a counterfeited tablet, an acceptance range of output values is established from the analysis unexpired authentic tablets.

Figure 7A:
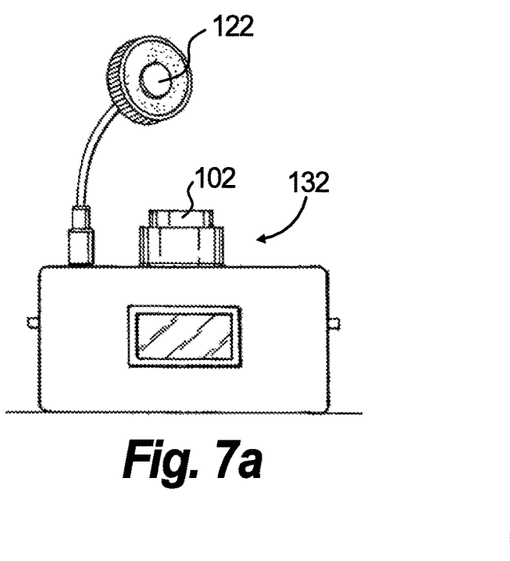
FIGS. 7a-7d illustrate a method to operate a prototype of the device of FIG. 1.
Figure 7B:
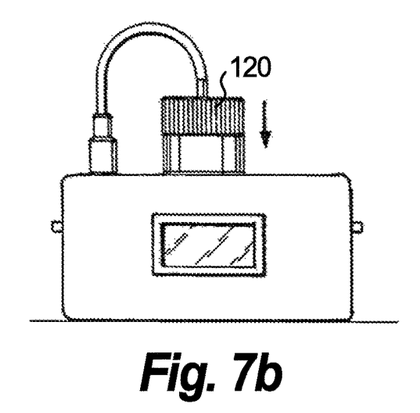
Figure 7C:
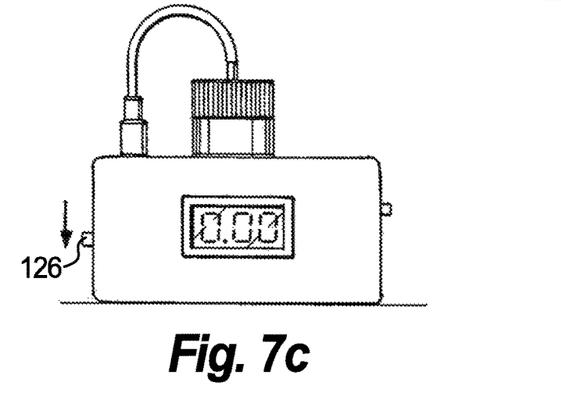
Figure 7D:
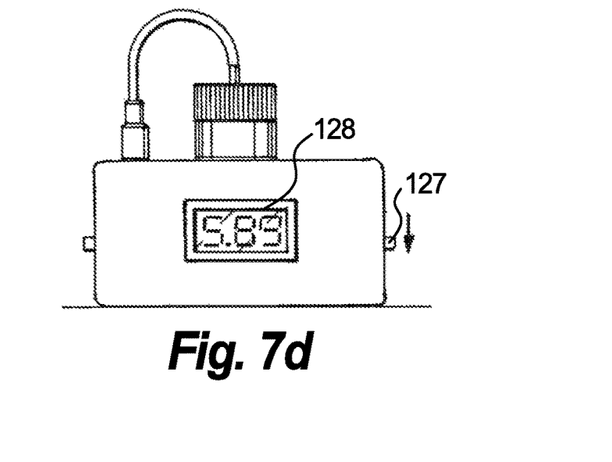

Now referring to FIGS. 7a-7d a series of method steps are shown to depict the device 100 for detection of suspected counterfeit pharmaceutical products in use. As shown in FIG. 6a, a user inserts the suspected counterfeit tablet 102 into the interface 132 with or without a filter placed adjacent to the photosensor 122. As shown in FIG. 7b, a cap portion of the light detector 120 is closed over the tablet 102. As shown in FIG. 7c, the on/off switch 126 for the light detector 120 is activated. A laser switch is activated by the on/off switch 127 and the digital output values with and without filters are recorded displayed on the visual display 128, as shown in FIG. 7c. A red indicator light may be active when the laser is on. The on/off switch 127 of the laser source simply activates the laser 110 and directs it to the suspected counterfeit tablet 102 concentrating the emitted light through the tablet 102 to the interface 132 of the laser detector 120. The digital output 128 is compared to a known digital number or range acceptable for authentic tablets. Based on this comparison the user immediately identifies whether the suspected tablet is a counterfeit or an authentic tablet.

Figure 6:
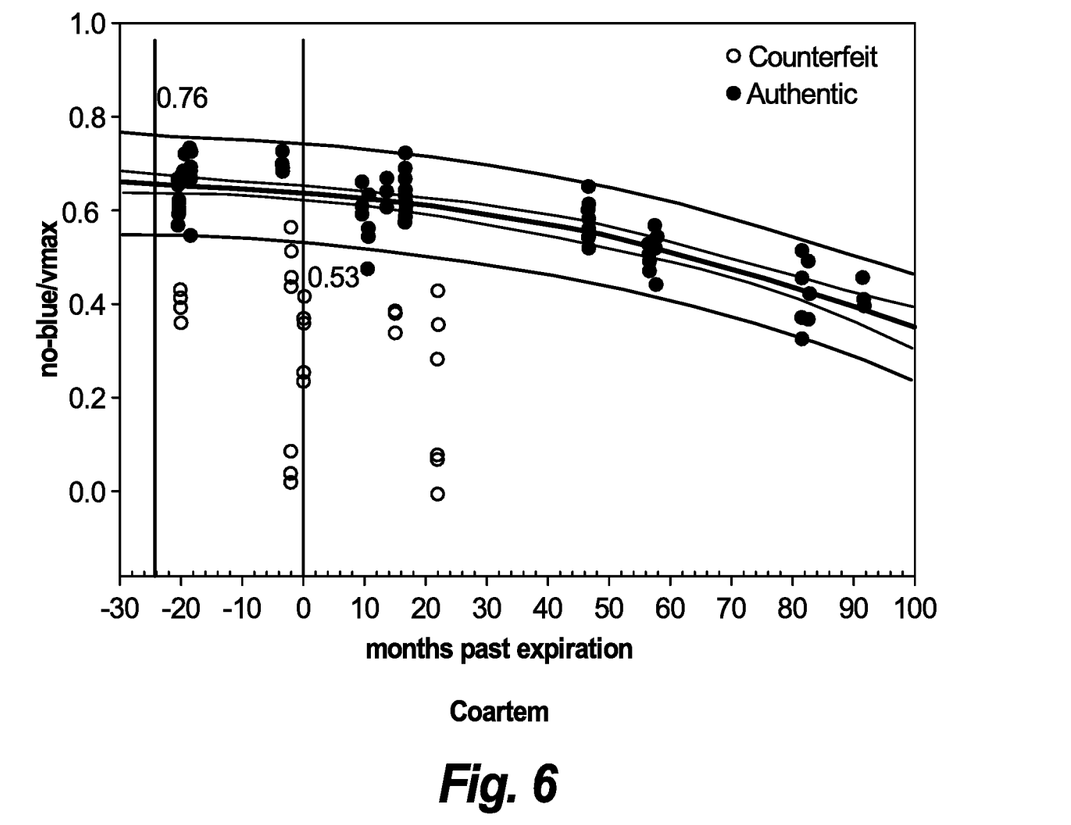
FIG. 6 is a plot of values derived from the device of FIG. 1 when detecting authentic expired and unexpired Coartem tablets, as well as counterfeited tablets.

The CoDI may also be used to identify very old tablets that have been repackaged with altered expiration dates. FIG. 6 shows a plot of values for a series of authentic expired and unexpired Coartem tablets. A range of accepted values for unexpired authentic tablets were determined. Any value outside the range (i.e. generally below the authentic range) is considered a counterfeit or has been expired for at least 6 years.

Figure 8:
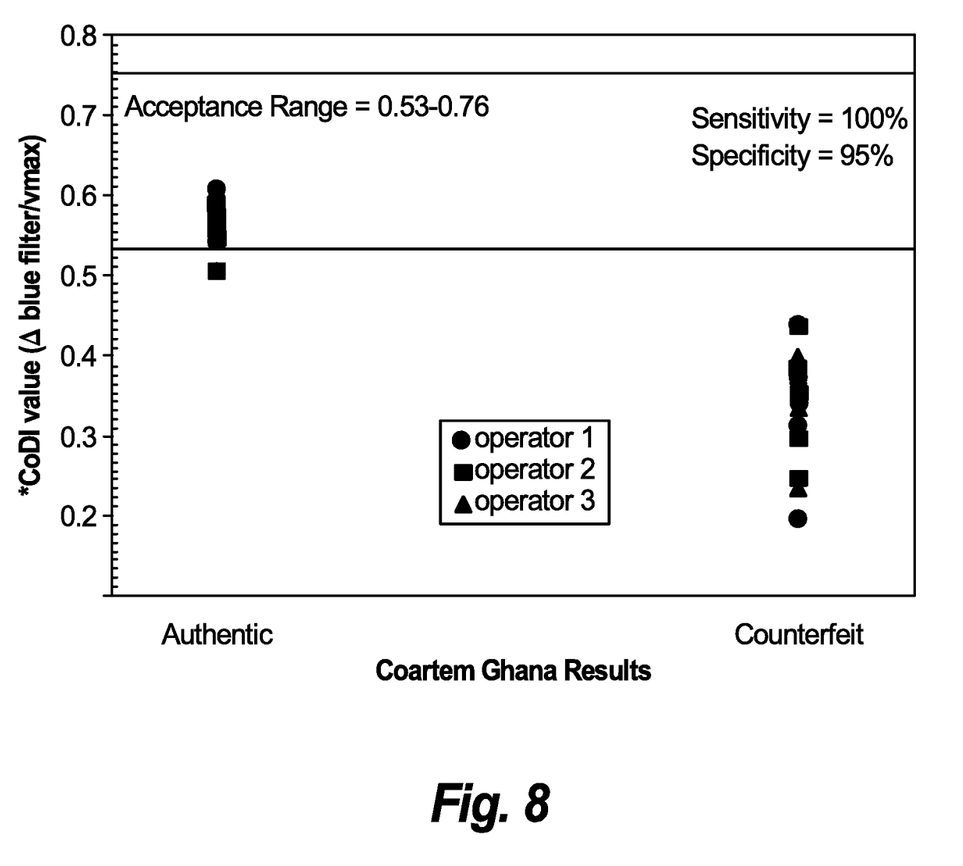
FIG. 8 is a graph illustrating the results obtained by using the device of FIG. 1 during a field test in Ghana.

The device 100 as described above was field-tested in Ghana. A set of 7 authentic and 5 counterfeited Coartem tablets were analyzed by 3 individuals blinded to the sample's status and briefly instructed on the operation of the device. Since the photoresistor used in this prototype is sensitive to temperature variability, the device values were adjusted for temperature effects (31° C. in Ghana vs ~25° at CDC). Statistical analysis showed a 100% sensitivity and 95% specificity (1 false positive) in predicting a counterfeit tablet (FIG. 8). Subsequent designs have incorporated a photodiode in place of a photoresistor to eliminate temperature effects.

INCORPORATION BY REFERENCE

All patents, published patent applications and other references disclosed herein are hereby expressly incorporated by reference in their entireties by reference.

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed is:

1. A portable device for measuring light transmission through a suspected counterfeit pharmaceutical tablet, the device comprising:
a sample tablet interface configured to secure a tablet, the sample tablet interface comprising a light-impervious member operable to surround a sample tablet;
a laser source configured to emit a light through the sample tablet; and
a light detector configured to receive a light transmission emanating from the sample tablet and measure an amount of light and color frequency passed through the sample tablet, wherein the amount of light passed through the sample tablet or the color frequency of light emitted is indicative of an authentic, counterfeit or degraded pharmaceutical tablet;
wherein the sample tablet interface is provided between the laser source and the light detector and is operable to block extraneous light around the periphery of a sample tablet from reaching the light detector.

2. The device of claim 1, wherein the amount of light measured through the suspected counterfeit pharmaceutical tablet is less than a known amount of light measured through an authentic sample indicates a counterfeit.

3. The device of claim 1, further comprising at least one color filter between the light detector and the sample tablet interface to condition the light emitted from the sample tablet, wherein the filter is selected for particular wavelength characteristics based on authentic tablets.

4. The device of claim 1, wherein the light detector includes a photo sensor in electronic communication with a meter configured to measure electrical current as a function of the light transmission and convert the measured light transmission to a digital output.

5. The device of claim 4, wherein the photo sensor is a CdS photoresistor or photodiode.

6. The device of claim 4, wherein the light detector includes a photoresister in electronic communication with an ohmmeter or digital voltmeter configured to measure the intensity of the light passed through the sample tablet.

7. The device of claim 1, wherein the light detector comprises a cap portion that is operable to contact the sample tablet interface and cover the sample tablet.

8. The device of claim 7, wherein the light-impervious member comprises an O-ring surrounding the sample tablet, and wherein the O-ring is configured to block extraneous light and concentrate light from the laser source to pass through the tablet.

9. The device of claim 1, wherein the sample tablet includes a molded and compressed solid dose pharmaceutical tablet.

10. The device of claim 1, wherein the light source includes a wavelength in the range of class Ma (<5 mW) or class IIIb (5-500 mW).

11. The device of claim 1, wherein the light detector includes an inlet configured to communicate with a power source.

12. The device of claim 1, further including a charged couple device configured for capturing digital images of tablets exposed to laser light along with image analysis software to determine authenticity based on intensity and color of light passing through the sample tablet.

13. The device of claim 1, wherein a change in color of light emitted from the sample tablet relative to an authentic tablet indicates a counterfeit or degraded tablet.

14. A method for measuring light transmission through a suspected counterfeit pharmaceutical tablet, the steps comprising: providing a device according to claim 1; directing the laser source towards a suspected counterfeit pharmaceutical tablet; and concentrating the emitted light transmission through the suspected counterfeit pharmaceutical tablet towards the laser detector; measuring the intensity of the light transmission through the suspected counterfeit pharmaceutical tablet using a photo sensor in electronic communication with a meter; and comparing the measured light intensity to a known intensity of an authentic tablet to determine the authenticity of the suspected counterfeit pharmaceutical tablet.

* * * * *